United States Patent
Wang et al.

(10) Patent No.: US 10,858,555 B2
(45) Date of Patent: Dec. 8, 2020

(54) ADHESIVE SYSTEM, METHOD OF MANUFACTURE THEREOF AND BIOLOGICAL KIT COMPRISING SAME

(71) Applicant: City University of Hong Kong, Kowloon Tong (HK)

(72) Inventors: Zuankai Wang, Hong Kong (HK); Yanhua Zhao, Hong Kong (HK); Yang Wu, Lanzhou (CN); Liang Wang, Changchun (CN)

(73) Assignee: CITY UNIVERSITY OF HONG KONG, Kowloon (HK)

( * ) Notice: Subject to any disclaimer, the term of this patent is extended or adjusted under 35 U.S.C. 154(b) by 436 days.

(21) Appl. No.: 15/622,196

(22) Filed: Jun. 14, 2017

(65) Prior Publication Data
US 2018/0362814 A1 Dec. 20, 2018

(51) Int. Cl.
C09J 167/04 (2006.01)
C09J 133/26 (2006.01)
A61L 24/04 (2006.01)
C09J 133/06 (2006.01)

(52) U.S. Cl.
CPC .......... *C09J 167/04* (2013.01); *A61L 24/043* (2013.01); *C09J 133/068* (2013.01); *C09J 133/26* (2013.01)

(58) Field of Classification Search
CPC .............................. C09J 133/02; C09J 167/04
See application file for complete search history.

(56) References Cited

FOREIGN PATENT DOCUMENTS

WO WO2008/002471 * 3/2008 ............... A61F 2/02

OTHER PUBLICATIONS

Waite, Herbert J., "Adhesion a' la Moule", Integr. Comp. Biol., 42:1172-1180 (2002).
Rose, et al., "Nanoparticle solutions as adhesives for gels and biological tissues", Nature, vol. 505, Jan. 16, 2014.
Selvapalam, et al., "Supramolecular Velcro for Reversible Underwater Adhesion", Angewandte Chemie International Edition, Mar. 2013.
Lee, et al., "Single-molecule mechanics of mussel adhesion", PNAS, vol. 103, No. 35, pp. 12999-13003, Aug. 29, 2006.
Heinzmann, et al., "Supramolecular polymer adhesives: advanced materials inspired by nature", Chem. Soc. Rev., 45, pp. 342-358, 2016.
Jones, et al., "Water-Borne Endovascular Embolics Inspired by the Undersea Adhesive of Marine Sandcastle Worms", Adv. Healthcare Mater., 5, pp. 795-801, 2016.

(Continued)

*Primary Examiner* — Dah-Wei D. Yuan
*Assistant Examiner* — Andrew J Bowman
(74) *Attorney, Agent, or Firm* — Melvin Li; Heslin Rothenberg Farley & Mesiti PC

(57) ABSTRACT

The present invention is concerned with an adhesive system. The system comprises a guest copolymer portion and a host copolymer portion. The guest copolymer portion includes 3,4-dihydroxy-L-phenylalanine (DOPA) acting as an adhesive moiety, a recognition molecule and a hydrophobic molecule connecting the adhesive moiety and the recognition molecule. The host copolymer portion includes a macrocyclic host molecule from a host family of supramolecules for specifically binding with the guest copolymer at the recognition molecule, and a polymer with temperature dependent wettability.

6 Claims, 17 Drawing Sheets
(14 of 17 Drawing Sheet(s) Filed in Color)

(56) References Cited

OTHER PUBLICATIONS

Lee, et al., "Mussel-Inspired Adhesives and Coatings", NIH Public Access, Author Manuscript, Annu. Rev. Mater Res., 41, pp. 99-132, Aug. 1, 2011.
Lee, et al., "Mussel-Inspired Surface Chemistry for Multifunctional Coatings", NIH Public Access, Author Manuscript, Science, 318 (5849), pp. 426-430, Oct. 19, 2007.
Fichman, et al., Seamless Metallic Coating and Surface Adhesion of Self-Assembled Bioinspired Nanostructures Based on Di-(3,4-dihydroxy-L-phenylalanine) Peptide Motif, ACS Nano, vol. 8, No. 7, pp. 7220-7228, 2014.
Lee, et al., "A reversible wet/dry adhesive inspired by mussels and geckos", Nature Publishing Group, vol. 448, Jul. 19, 2007.
Ahn, et al., "High-performance mussel-inspired adhesives of reduced complexity", Macmillan Publishers Limited, Nature Communications, Oct. 19, 2015.
North, et al., "High Strength Underwater Bonding with Polymer Mimics of Mussel Adhesive Proteins", ACS Publications, Applied Materials & Interfaces, 9, 7866-7872, 2017.
Lim, et al. "Nanomechanics of Poly(catecholamine) Coatings in Aqueous Solutions", Angewandte Chemie, Feb. 2016.
Shin, et al., "Complete prevention of blood loss with self-sealing haemostatic needles", Nature Materials, vol. 16, Jan. 2017.
Yang, et al., "A Bio-Inspired Swellable Microneedle Adhesive for Mechanical Interlocking with Tissue", HHS Public Access, Nat. Commun., Oct. 16, 2013.
Zeng, et al., "Adhesion and Detachment Mechanisms between Polymer and Solid Substrate Surfaces: Using Polystyrene—Mica as a Model System", Macromolecules, ACS Publications, 49, pp. 5223-5231, 2016.
Zhao, et al. "Underwater contact adhesion and microarchitecture in polyelectrolyte complexes actuated by solvent exchange", HHS Public Access, Nat. Mater. 15(4), pp. 407-412, Apr. 2016.
Maier, et al., "Adaptive synergy between catechol and lysine promotes wet adhesion by surface salt displacement", Science, 349, pp. 628-632, 2015.
Kim, et al., "Stooped Nanohairs: Geometry-Controllable Unidirectional, Reversible, and Robust Gecko-like Dry Adhesive", Advanced Materials, 21, pp. 2276-2281, 2009.
Michal, et al., "Stimuli-Responsive Reversible Two-Level Adhesion from a Structurally Dynamic Shape-Memory Polymer", Applied Materials & Interfaces, 8, 11041-11049, 2016.
Wang, et al., "Switchable Dry Adhesion with Step-like Micropillars and Controllable Interfacial Contact", ACC Publications, ACS Appl. Mater. Interfaces, 8, pp. 10029-10037, 2016.
Ye, et al., "Phase Change of Gallium Enables Highly Reversible and Switchable Adhesion", Advanced Materials, May 2016.
Reddy, et al., "Bioinspired Surfaces with Switchable Adhesion**", Advanced Materials, 19, 3833-3837, 2007.
Narkar, et al., "pH Responsive and Oxidation Resistant Wet Adhesive based on Reversible Catechol-Boronate Complexation", American Chemical Society, Chemistry of Materials, 28, 5432-5439, 2016.
Zeng, et al., "Strong reversible $FE^{3+}$-mediated bridging between dopa-containing protein films in water", PNAS, vol. 107, No. 29, pp. 12850-12853, Jul. 20, 2010.
Zhong, et al., "Self-Assembling Multi-Component Nanofibers for Strong Bioinspired Underwater Adhesives", HHS Public Access, 9(10), pp. 858-866, Oct. 9, 2014.
Deshmukh, et al., "Role of Solvation Dynamics and Local Ordering of Water in Inducing Conformational Transitions in Poly(N-isopropylacrylamide) Oligomers through the LCST", ACS Publications, J. Phys. Chem., 116, pp. 2651-2663, 2012.
Abbott, et al., "Single Chain Structure of a Poly(N-isopropylacrylamide) Surfactant in Water", The Journal of Physical Chemistry, 119, pp. 3837-3845, 2015.
Puthoff, et al., "Changes in material properties explain the effects of humidity on gecko adhesion", Journal of Experimental Biology, Nov. 2010.
Stark, et al., "Surface wettability plays a significant role in gecko adhesion underwater", PNAS, vol. 110, No. 16, Apr. 16, 2013.

* cited by examiner

FIG. 3A
FIG. 3B
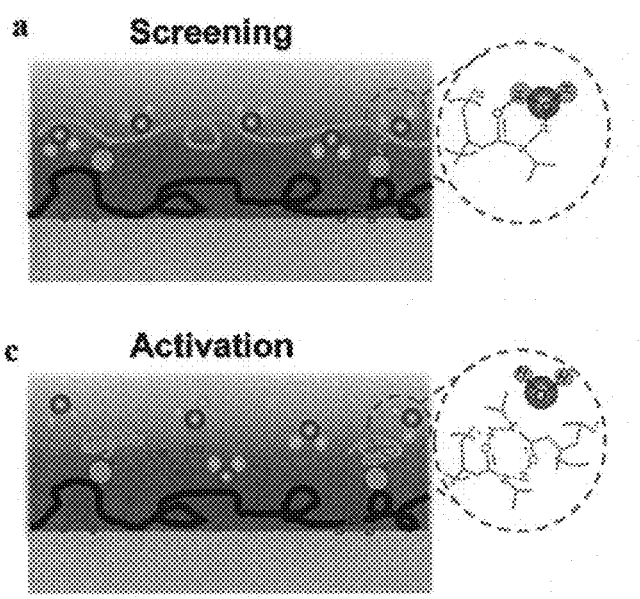
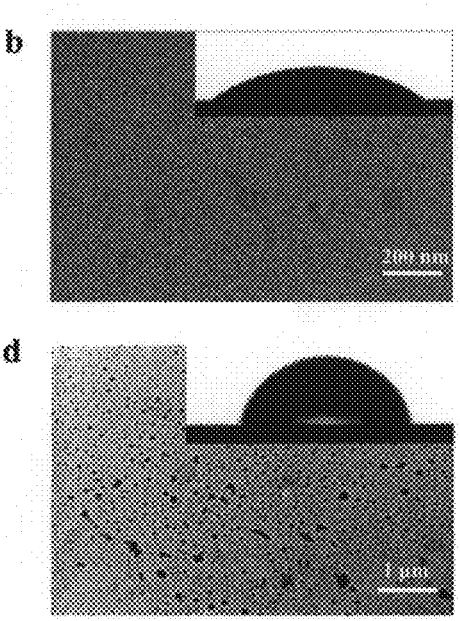
FIG. 3C
FIG. 3D

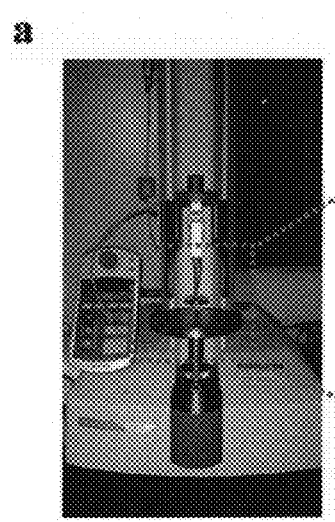 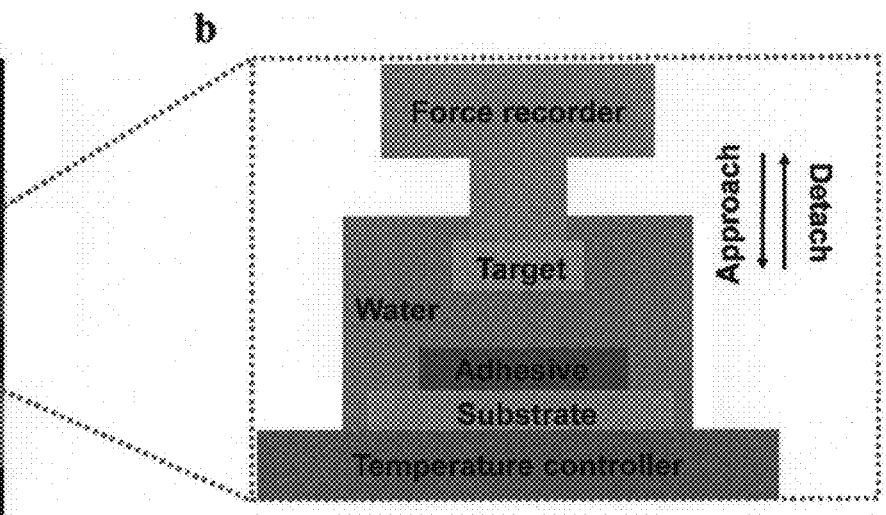
FIG. 9A                    FIG. 9B

ADHESIVE SYSTEM, METHOD OF MANUFACTURE THEREOF AND BIOLOGICAL KIT COMPRISING SAME

FIELD OF THE INVENTION

The present invention is concerned with an adhesive system, and in particular an adhesive system with reversible and temperature-dependent adhesive characteristics in a wet environment, e.g. under water. The present invention is also concerned with a kit, e.g. a biological kit such as a surgical kit, comprising such an adhesive system, and methods of manufacture thereof.

BACKGROUND OF THE INVENTION

Most existing commercial glues or adhesiveness work on a limited range of target surfaces and in the absence of water. Once water, or a wet environment, is set in, adhesive behavior of such glues tend to be disrupted. The breakdown of contact adhesion of such glues as a result of the adsorption of lubricating water molecules between their interfaces impacts a wide range of contexts, such as water pipeline leakage, corrosion of hull and artificial teeth take off.

The rational design of smart surfaces with switchable adhesive properties in a wet environment has remained a formidable challenge in the adhesion science and materials engineering. Despite intense demand in various commercial and industrial applications and exciting progress in mimicking the remarkable wet adhesion through the exquisite control of catechol chemistry, polyelectrolyte complex and supramolecular architectures, the full recapitulation of nature's dynamic function is still limited.

The present invention seeks to address the limitations of conventional adhesive systems, or at least to provide a useful alternative to the public. For example, the present invention provides an adhesive system with reversible and temperature-dependent adhesive characteristics in a wet environment, e.g. under water. The present invention is also concerned with a kit, e.g. a biological kit such as a surgical kit, comprising such an adhesive system, and methods of manufacture thereof.

SUMMARY OF THE INVENTION

According to a first aspect of the present invention, there provided an adhesive system operable in a wet environment and with temperature-dependent adhesiveness characteristics, comprising a guest copolymer portion and a host copolymer portion reversibly bindable with the guest copolymer portion, wherein:
 the guest copolymer portion including 3,4-dihydroxy-L-phenylalanine (DOPA) acting as an adhesive moiety, a recognition molecule and a hydrophobic molecule connecting the adhesive moiety and the recognition molecule;
 the host copolymer portion including a macrocyclic host molecule from a host family of supramolecules for specifically binding with the guest copolymer at the recognition molecule, and a polymer with temperature dependent wettability;
 the guest copolymer portion and the host copolymer portion are adapted to assume a first configuration in which the guest copolymer portion and the host copolymer portion are bonded together and, at or below a predetermined temperature, the adhesive moiety of the guest copolymer is screened by a water layer absorbed by a chain from the temperature dependent wettability polymer, thus hindering adhesiveness of the adhesive system; and
 the guest copolymer portion and the host copolymer portion are adapted to assume a second configuration in which, at a temperature above the predetermined temperature, the adhesive moiety of the guest copolymer is not screened by water due to collapsing of the chain of the temperature dependent wettability polymer, thus releasing the adhesive moiety of the guest copolymer in order to allow the adhesiveness of the adhesive system to emerge.

Preferably, the recognition molecule may be selected from the group consisting of adamantine (AD), aminomethylferrocene (FC), 8-anilino-1-naphthalenesulfonic acid ammonium salt (ANS) and azobenzene (AZO), and the hydrophobic molecule is methoxyethyl acrylate (MEA). Specifically, the recognition molecule may be adamantine (AD) or ammonium salt (ANS).

Advantageously, the macrocyclic host molecule may be cyclodextrin (CD) or cucurbituril (CB).

Suitably, the temperature-dependent wettability polymer may be selected from the group consisting of poly(N-isopropylacrylamide) (p-NIPAM), poly(N,N-diethyl acrylamide) (p-DEAAM), poly(N-(D L)-(1-hydroxymethyl) propylmethacrylamide) (p-(DL)-HMPMA), poly(dimethylaminoethyl methacrylate) (p-DMAEMA), and poly(N-vinylcaprolactone) (p-VCL). In particular, the temperature-dependent wettability polymer may be poly(N-isopropylacrylamide) (p-NIPAM).

The predetermined temperature may be dependent on the ratio of poly(N-isopropylacrylamide) (p-NIPAM) to cyclodextrin (CD) in the host copolymer. In an embodiment, the ratio of poly(N-isopropylacrylamide) (p-NIPAM) to cyclodextrin (CD) may be substantially 150:1 (n:n, molar ratio), whereby the predetermined temperature may be substantially 35° C.

The system may be adapted with an adhesiveness characteristic independent surrounding pH condition.

According to a second aspect of the present invention, there is provided a method of manufacture of an adhesive system as described above.

According to a third aspect of the present invention, there is provided a method of manufacture of an adhesive system operable in a wet environment and with temperature-dependent adhesiveness characteristics, the system including a guest copolymer portion and a host copolymer portion, comprising the steps of:
 free radical copolymerization of 3,4-dihydroxy-L-phenylalanine (DOPA) acting as an adhesive moiety, a recognition molecule selected from the group consisting of adamantine (AD), aminomethylferrocene (FC), 8-anilino-1-naphthalenesulfonic acid ammonium salt (ANS) and azobenzene (AZO), and methoxyethyl acrylate (MEA) acting as a hydrophobic molecule in an inert gas environment; and
 co-polymerization of cyclodextrin (CD) and a temperature-dependent wettability polymer selected from the group consisting of poly(N-isopropylacrylamide (p-NIPAM), poly(N,N-diethyl acrylamide) (p-DEAAM), poly(N-(D L)-(1-hydroxymethyl) propylmethacrylamide) (p-(DL)-HMPMA), poly(dimethylaminoethyl methacrylate) (p-DMAEMA), and poly(N-vinylcaprolactone) (p-VCL).

According to a fourth aspect of the present invention, there is provided a method of manufacture of a biological kit with a first substrate for reversible and temperature dependent adhesion to a second substrate in a wet environment, comprising the steps of:

dip-coating the first substrate with a guest copolymer portion, the guest copolymer portion including 3,4-dihydroxy-L-phenylalanine (DOPA) acting as an adhesive moiety, a recognition molecule and a hydrophobic molecule connecting the adhesive moiety and the recognition molecule;

immersing the dip-coated first substrate in a host copolymer portion, the host copolymer portion including a macrocyclic host molecule for specifically binding with the guest copolymer at the recognition molecule and a polymer with temperature dependent wettability, wherein the first substrate is made of a material selected from a group of inorganic or organic materials including silicon, glass, titanium, aluminum, polydimethylsiloxane (PDMS) and polytetrafluoroethylene (PTFE).

Preferably, the recognition molecule may be selected from the group consisting of adamantine (AD), aminomethylferrocene (FC), 8-anilino-1-naphthalenesulfonic acid ammonium salt (ANS) and azobenzene (AZO), and the hydrophobic molecule is methoxyethyl acrylate (MEA). In particular, the recognition molecule may be adamantine (AD) or ammonium salt (ANS).

Advantageously, the macrocyclic host molecule may be cyclodextrin (CD) or cucurbituril (CB).

Suitably, the temperature-dependent wettability polymer may be selected from the group consisting of poly(N-isopropylacrylamide) (p-NIPAM), poly(N,N-diethyl acrylamide) (p-DEAAM), poly(N-(D L)-(1-hydroxymethyl) propylmethacrylamide) (p-(DL)-HMPMA), poly(dimethylaminoethyl methacrylate) (p-DMAEMA), and poly(N-vinylcaprolactone) (p-VCL). In an embodiment, the temperature-dependent wettability polymer may be poly(N-isopropylacrylamide (p-NIPAM).

The molar ratio of poly(N-isopropylacrylamide (p-NIPAM) to cyclodextrin (CD) may be substantially 150:1.

BRIEF DESCRIPTION OF THE DRAWINGS

The patent of application file contains at least one drawing executed in color. Copies of this patent or patent application publication with color drawing(s) will be provided by the Office upon request and payment of the necessary fee.

Some embodiments of the present invention will now be explained, with reference to the accompanied drawings, in which:—

FIGS. 3A to 3D illustrate the mechanism of reversible and temperature-dependent adhesion of the adhesive system of FIGS. 1A to 1D;

FIGS. 5A and 5B shown synthetic schemes of the guest and host copolymers, in which FIG. 5A shows a guest copolymer pDOPA-AD-MEA synthesized via free radical polymerization of AD monomer, DOPA monomer and MEA, and FIG. 5B shows the preparation of host copolymer pNIPAM-CD by the copolymerization of NIPAM and CD;

FIG. 8B shows an additional intense C1s absorption peak at 288.3 eV corresponding to the carbonyl amide group in pNIPAM-CD emerges upon the successful assembly of the adhesive coating;

FIGS. 9A and 9B are an image and a representation showing a UTM setup to measure the interfacial adhesion, in which FIG. 9A is an optical photograph of the UTM, and FIG. 9B is a schematic drawing showing the detailed set-up to characterize the interfacial adhesion;

DETAILED DESCRIPTION OF PREFERRED EMBODIMENTS OF THE INVENTION

The present invention is concerned with a radically new approach to synthesize a versatile adhesive system. This adhesive system, or "smart" adhesive system, entails a reversible, tunable and fast regulation of wet adhesion on diverse surfaces. By smart adhesive system, it refers to the ability of the adhesive system, or adhesive interface or coating, to engage in providing on-demand adhesiveness, or non-adhesiveness, in a wet environment and depending on the surrounding temperature. More particularly, the wet adhesive system synergistically takes advantage of host-guest molecular interaction, adhesive nature of catechol chemistry and stimuli-responsive polymer, thus allowing for the on-demand screening and activation of interfacial interaction simply in response to a local temperature trigger. The present invention represents an important paradigm in the design of smart underwater adhesive, and can also be incorporated in the design of bio-materials. For example, adhesive systems in accordance with the present invention can be used in bio-implants, surgeries, etc. in the arena of medical and reconstructive surgeries.

The following will depict the present invention including the fabrication of a universal adhesive that renders a reversible, dynamic, fast regulation of underwater adhesion. The present invention leverages on the synergistic cooperation of catechol chemistry, responsive wettability as well as selective host-guest interaction, which confers control over properties in a reversible, highly tunable, dynamic fashion. Moreover, we demonstrate that our biomimetic adhesive can be applied to various substrates and display superior adhesion properties.

One embodiment of the present invention is concerned with the use of 3,4-dihydroxy-L-phenylalanine (DOPA) polymer, a guest moiety adamantine (AD) and methoxyethyl acrylate (MEA) monomer to form a guest copolymer portion. This copolymer portion of the adhesive system may be referred as pDOPA-AD-MEA. Then a host copolymer portion is prepared by conjugating poly(N-isopropylacrylamide) (pNIPAM) and cyclodextrin (CD), thus forming (pNIPAM-CD). In the host copolymer portion, pNIPAM serves as a temperature trigger element and CD, or β-cyclodextrin (β-CD) is a host molecule designed for selective binding with the guest copolymer portion.

Figure 1A:
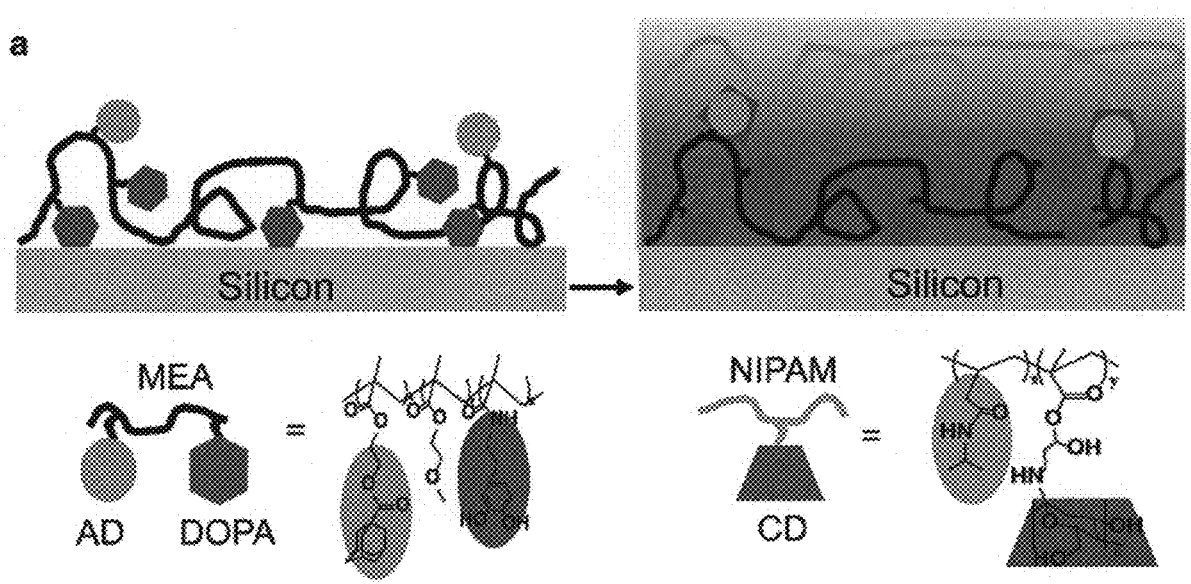
FIGS. 1A, 1B, 1C and 1D illustrate the synthesis and characterization of an embodiment of a wet adhesive system in accordance with the present invention.

In one embodiment, the guest copolymer portion may first be applied on a substrate made of, e.g. silicon, by dip-coating. The silicon substrate applied with the guest copolymer portion is then assembled with the host copolymer portion due to self-assembly of the host copolymer and specific host-guest chemistry. Please see FIG. 1A. FIG. 1A is a schematic diagram showing elements of the adhesive system and steps of synthesizing the adhesive system. The synthesis process involves the production of the adhesive guest copolymer pDOPA-AD-MEA on a clean silicon substrate using a dip-coating methodology as mentioned above, followed by the self-assembly of the host copolymer pNIPAM-CD using the host-guest molecular recognition.

A more detailed illustration of the adhesive system and its characterization is shown in FIGS. 5A to 7B.

Figure 5A:
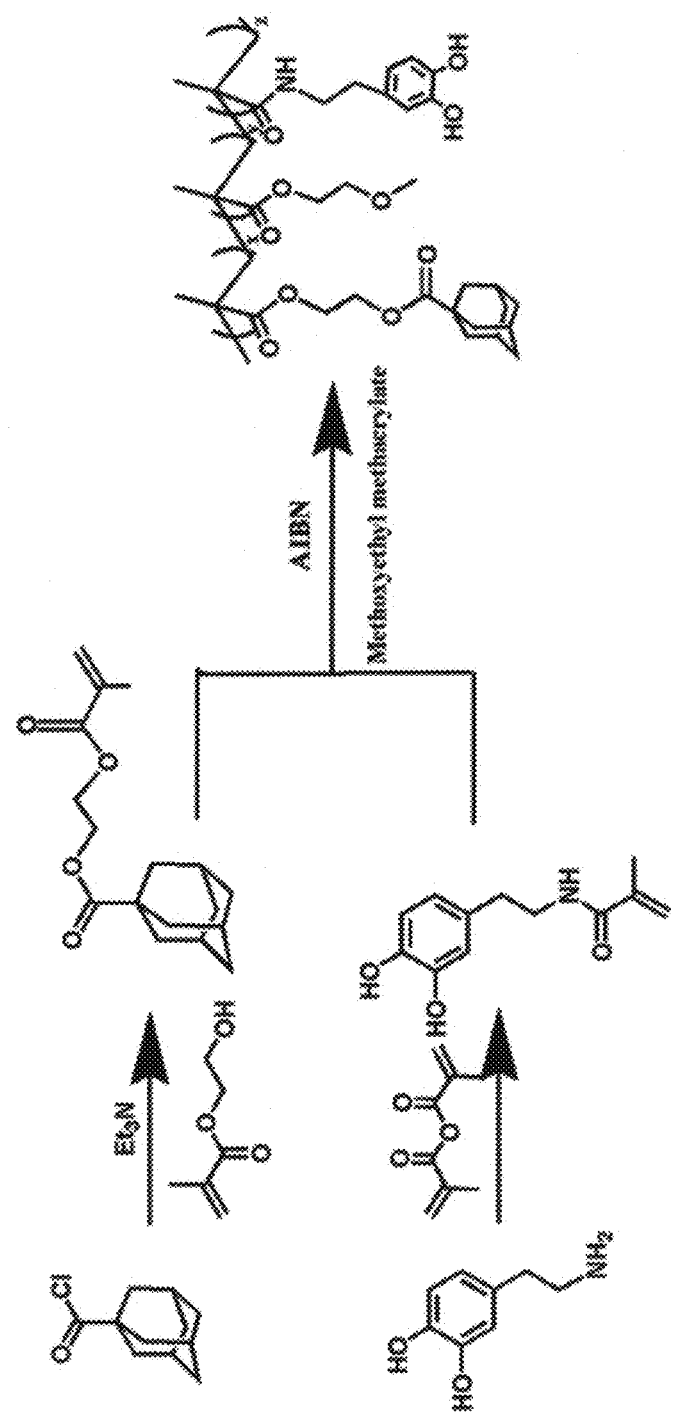
Figure 5B:
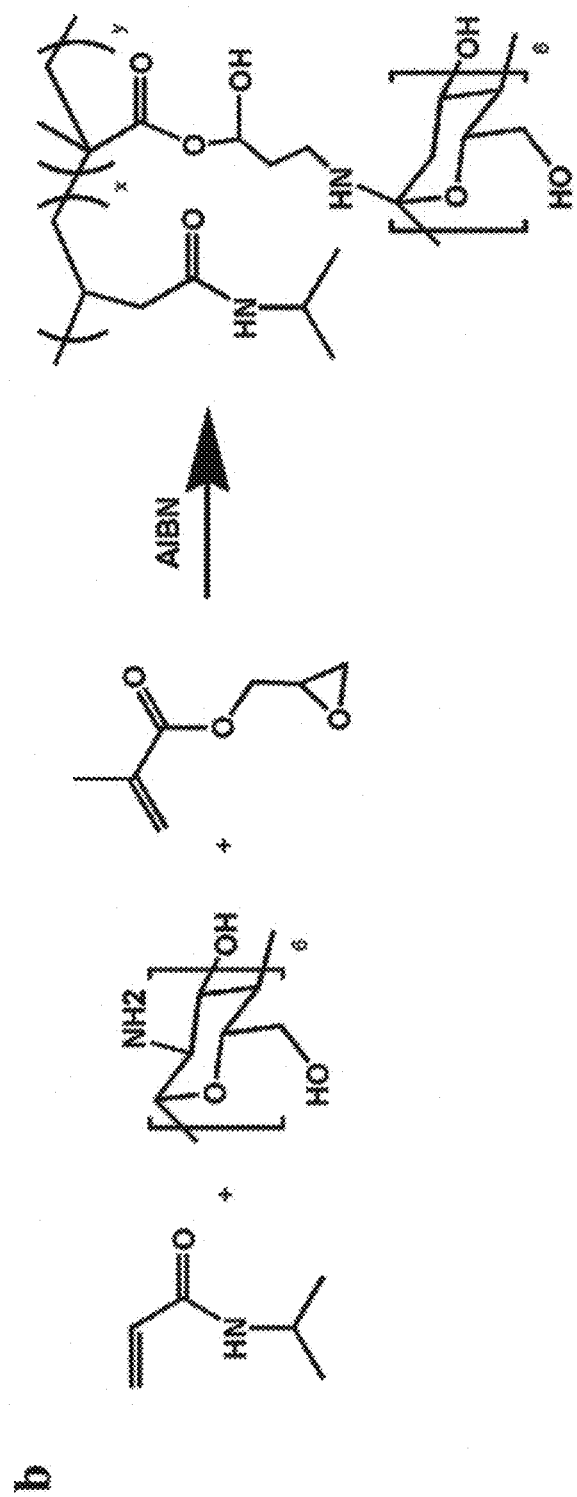

FIGS. 5A and 5B are the schemes of the fabrication process of the guest and host copolymers. The detailed fabrication process is illustrated in the supporting information. FIGS. 5A and 5B shown synthetic schemes of the guest and host copolymers. FIG. 5A illustrates that the DOPA monomer was synthesized from DOPA-HCl and the AD monomer was prepared with adamantanecarboxylic acid chloride in anhydrous methylene chloride. Then the guest copolymer pDOPA-AD-MEA was synthesized via free radical polymerization of AD monomer, DOPA monomer and MEA. FIG. 5B shows the preparation of host copolymer pNIPAM-CD by the copolymerization of NIPAM and CD.

Figure 6A:
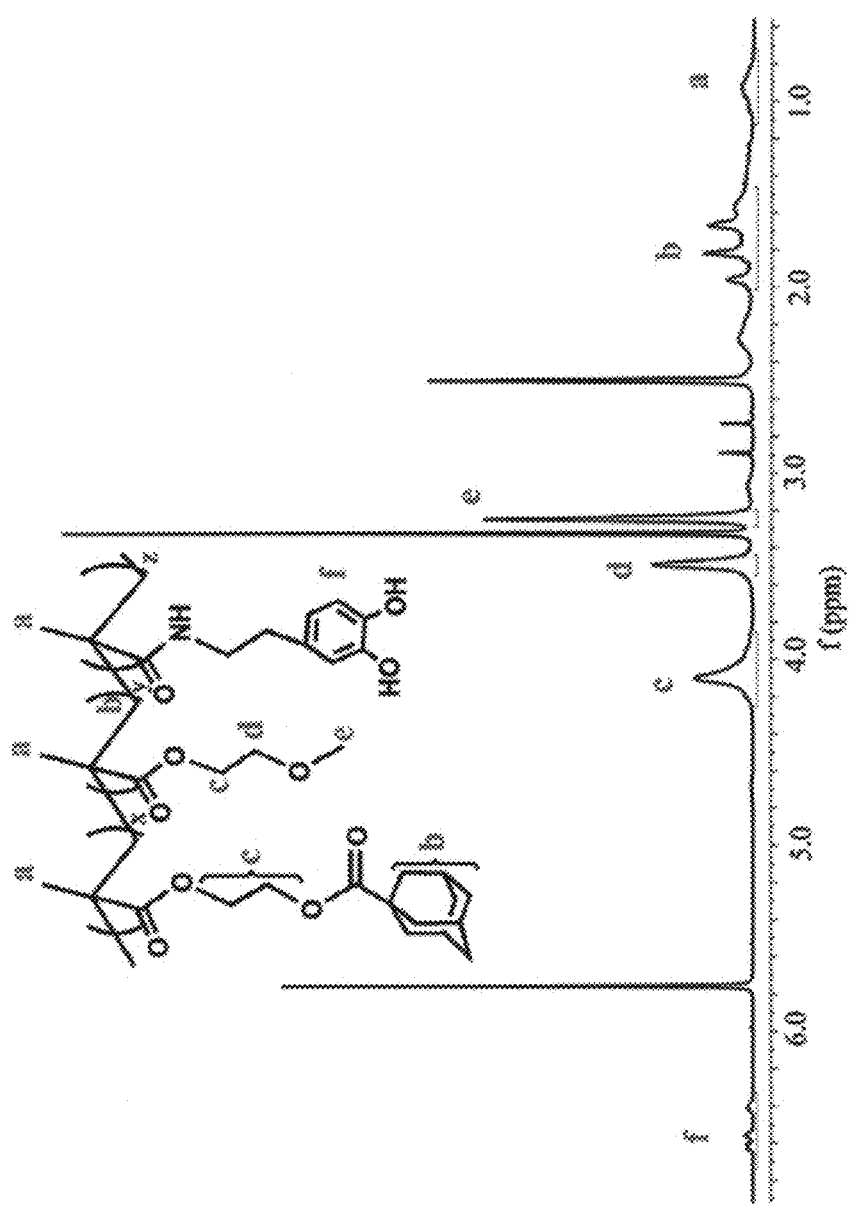
FIGS. 6A and 6B are graphs showing the $^1$H NMR spectrum of the guest copolymer pDOPA-AD-MEA and host copolymer pNIPAM-CD, respectively, in DMSO, in which the characteristic NMR peaks corresponding to pDOPA-AD-MEA and pNIPAM-CD are labeled.
Figure 6B:
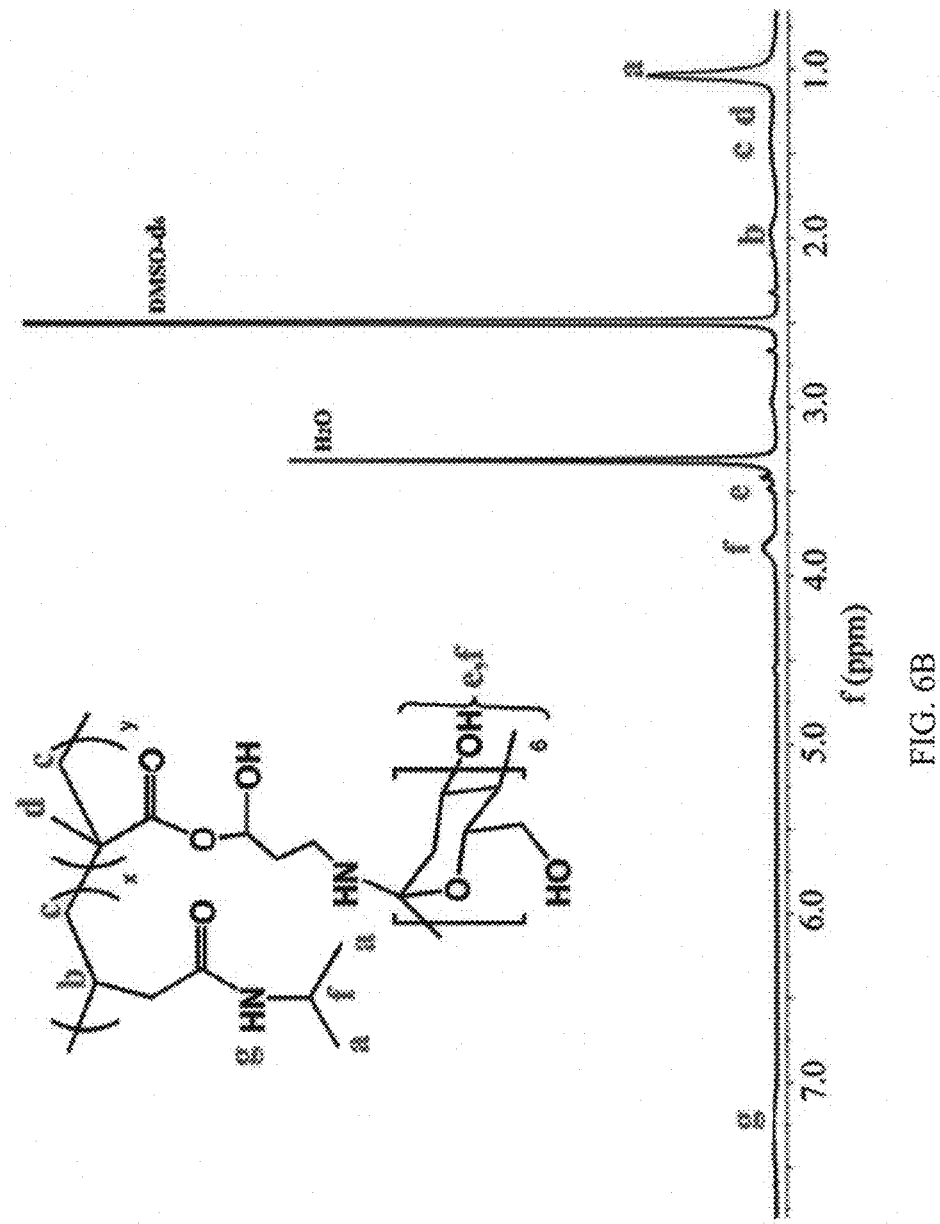

FIGS. 6A and 6B are the $^1$H NMR spectrums of the guest copolymer pDOPA-AD-MEA and host copolymer pNIPAM-CD, respectively, in DMSO, in which the functional chemical structures of the host and guest copolymers as well as their corresponding NMR peaks are labeled. The characteristic NMR peak of adamantine group (b, 1.8 ppm) and phenolic hydroxyl group (f, 6.6 ppm) in the pDOPA-AD-MEA can be easily identified (FIG. 6A). Similarly, FIG. 6B shows the characteristic NMR peaks of the pNIPAM-CD, which contains the cyclodextrin hydroxyl group (e, 3.5 ppm and f, 3.8 ppm) and imino group (7.25 ppm).

Figures 7A, 7B:
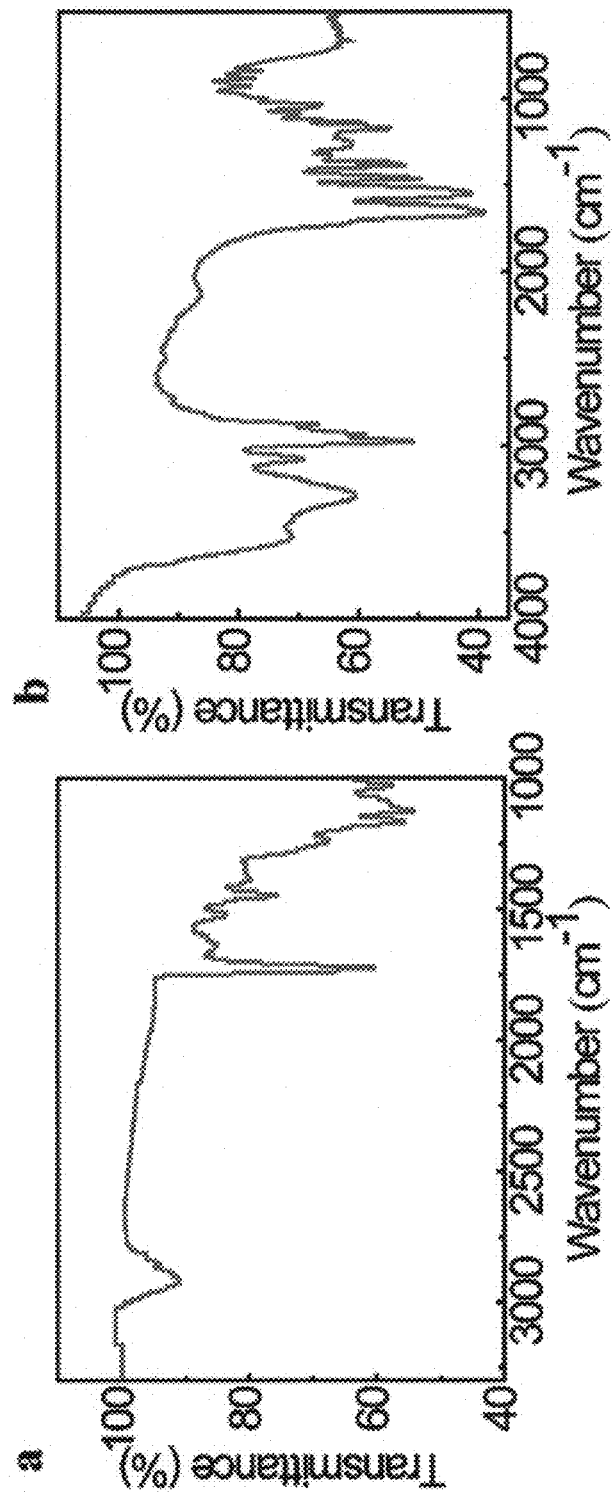
FIGS. 7A and 7B are graphs showing FTIR spectra of the guest copolymer pDOPA-AD-MEA and host copolymer pNIPAM-CD, respectively, in that in FIG. 7A, the characteristic absorption peaks corresponding to the phenolic hydroxyl group, ester acyl group, and benzene group are clearly illustrated, suggesting the successful synthesis of the pDOPA-AD-MEA, and in FIG. 7B the characteristic absorption peaks assigned to the cyclodextrin hydroxyl group, methyl-methylene group, carbonyl group, and imino group are shown to demonstrate the successful fabrication of the pNIPAM-CD.

FIGS. 7A and 7B are the (Fourier transform infrared spectroscopy) FTIR spectra of the guest copolymer pDOPA-AD-MEA (A) and host copolymer pNIPAM-CD (B) respectively, in that in FIG. 7A, the characteristic absorption peaks corresponding to the phenolic hydroxyl group (3430 $cm^{-1}$), ester acyl group (1730 $cm^{-1}$), and benzene group (1170 $cm^{-1}$) are clearly illustrated, suggesting the successful synthesis of the pDOPA-AD-MEA, and in FIG. 7B the characteristic absorption peaks assigned to the cyclodextrin hydroxyl group (3290 $cm^{-1}$), methyl-methylene group (2970 $cm^{-1}$), carbonyl group (1660 $cm^{-1}$), and imino group (1560 $cm^{-1}$) are shown to demonstrate the successful fabrication of the pNIPAM-CD;

As explained above, one characteristic of the present adhesive system is its ability for the adhesiveness engaged in a wet environment depending on the temperature or surrounding temperature. Specifically, the adhesiveness will kick in at or above a certain temperature, or a lower critical solution temperature (LCST). This LCST can be controlled by adjusting the ratio of pNIPAM to CD monomer in the host copolymer portion (pNIPAM-CD). As an example, when the ratio of pNIPAM to CD monomer is 150:1 (n:n), the LCST is measured to be substantially 35° C. The ratio is molar ratio, it's in n:n.

Figure 1B:
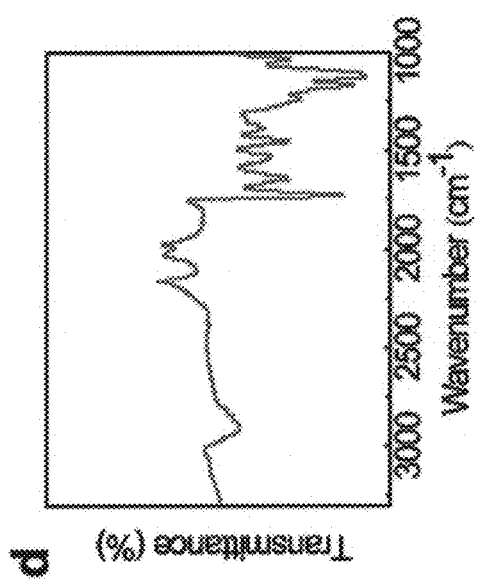
Figure 1C:
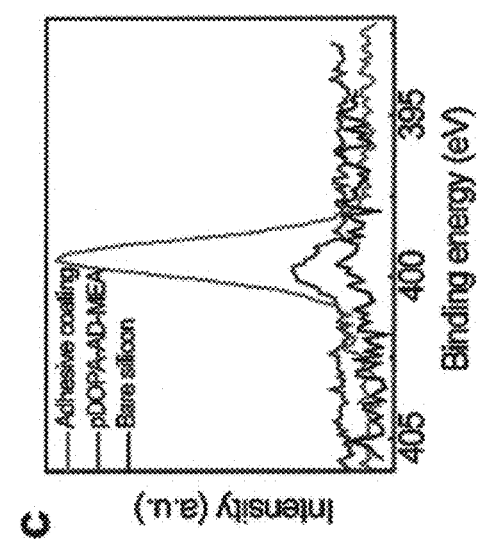

As explained above, the adhesive system can be applied on a substrate by dip-coating. The successful decoration and coating of the substrate with the adhesive system is evidenced by chemical composition analysis using the X-ray photoelectron spectroscopy (XPS) and attenuated total reflection infrared spectroscopy (AT-IR). Please see FIG. 1B (and FIG. 1C). FIGS. 1B and 1C are graphs of X-ray photoelectron spectroscopy (XPS) analysis of the chemical composition of the silicon substrate surface, adhesive guest copolymer pDOPA-AD-MEA as well as the adhesive coating, demonstrating the successful synthesis of the as-prepared adhesive. Specifically, in FIG. 1B, it is shown that it is shown that the intense peaks at 99.8 eV and 150.1 eV are ascribed to Si 2p and 2s signals for the bare silicon substrate. After coating with the adhesive guest copolymer pDOPA-AD-MEA on the silicon substrate, the Si signals are vanished and instead a weak N 1s peak at 399.5 eV emerges, which is assigned to the DOPA group. By contrast, the N 1s peak observed on the adhesive coating is much stronger, indicating the successful assembly of pNIPAM-CD onto the adhesive guest copolymer through the host-guest interaction. Please see FIG. 1C. Careful inspection of the content ratios of N element in the adhesive coating relative to that in the guest copolymer also confirms the successful self-assembly of the stimuli-responsive host copolymer. Please see FIGS. 8A and 8B, and below Table 1.

TABLE 1

Element content analysis of bare silicon, pDOPA-AD-MEA, and adhesive coating

| Element content (%) | C | O | N |
|---|---|---|---|
| Bare Si | 31.41 | 68.59 | 0 |
| pDOPA-AD-MEA | 72.63 | 27.04 | 0.89 |
| Adhesive coating | 71.63 | 24.04 | 3.83 |

Figure 1D:
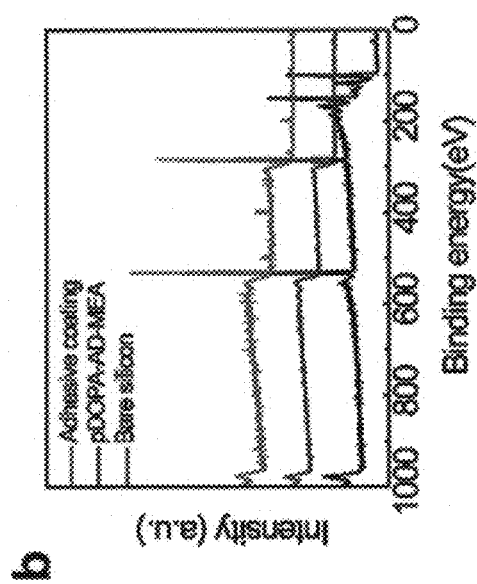

In addition, the ATIR spectra of the adhesive coating clearly shows the presence of the characteristics peaks of DOPA and pNIPAM. Please see FIG. 1D. FIG. 1D is a graph showing the AT-IR spectrum of a coating of the adhesive system, and the spectrum at 1630 cm$^{-1}$, 1525 cm$^{-1}$, 1380 cm$^{-1}$ and 1365 cm$^{-1}$ assigned to benzene and methyl group on pNIPAM, which demonstrates the presence of DOPA and pNIPAM, respectively. This demonstrates the successful coating of the adhesive system on the substrate.

Figure 2A:
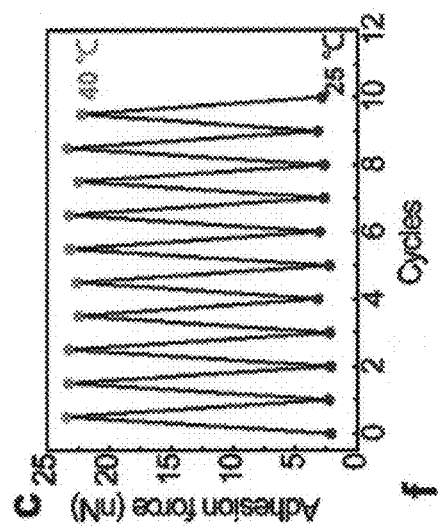
FIGS. 2A, 2B, 2C, 2D, 2E, 2F and 2G illustrate characterization of the adhesion system of FIGS. 1A to 1D.
Figure 2B:
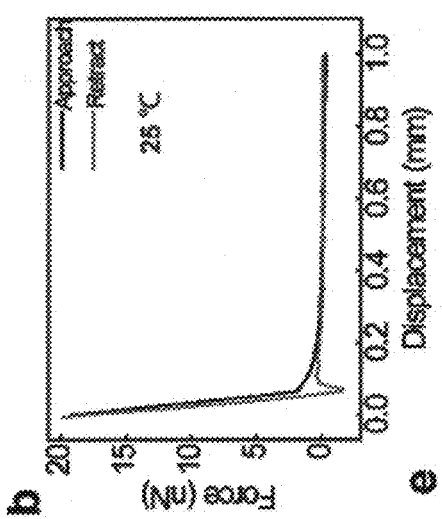
Figure 2C:
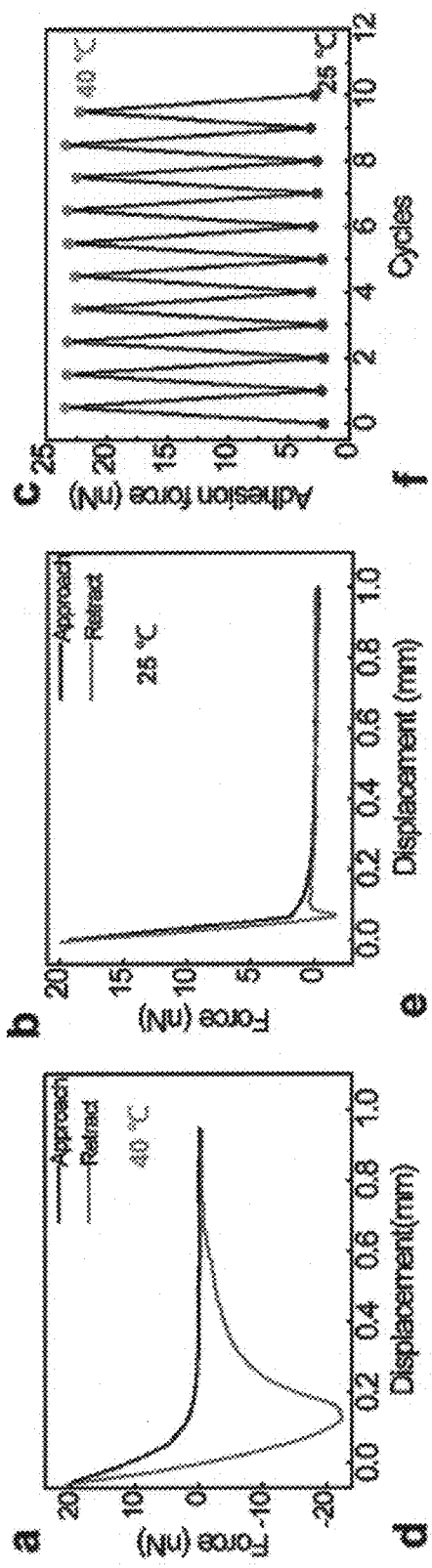
Figure 2D:
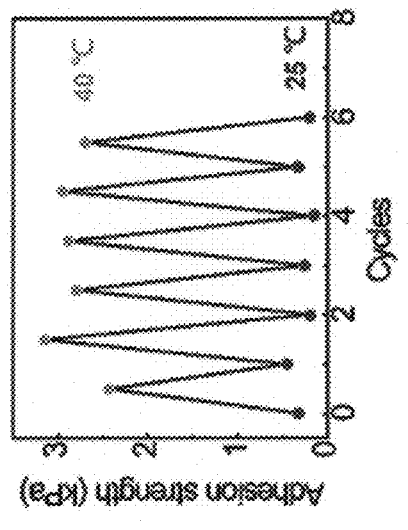
Figure 2E:
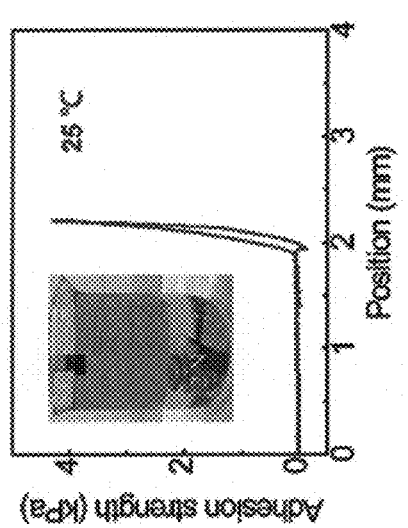

The wet adhesion property of the as-prepared adhesive system coated on the substrate was then determined by using an atomic force microscope (AFM) decorated with a temperature controller. Given a local temperature of the adhesive surface (40° C. in this case) above LCST, the adhesion force is measured to be ~23 nN. Please see FIG. 2A. FIG. 2A and FIG. 2B (and FIG. 2G) are graphs showing atomic force microscope (AFM) measurement of the wet adhesion force of the as-fabricated adhesive system on silicon substrate at 40° C. (a) and 25° C. (b), respectively. Referring to FIG. 2B, when the adhesive surface temperate is reduced to be below LCST (25° C.), the interfacial adhesion is deactivated and gives a minimal force of ~2.2 nN. The distinct adhesion capability in response to different temperatures is also reflected by the large contrast in the retraction distance shown in FIG. 2A (and FIG. 2G) and FIG. 2B. Noticeably, upon raising the adhesive temperature above LCST again, the interfacial adhesion is reactivated and exhibits a full reversible (adhesive) signature. FIG. 2C is a graph demonstrating reversible control of underwater adhesion by tuning or adjusting the surface temperature. As shown in FIG. 2C, there is no notable degradation in the adhesion strength based on 10 cycles of measurement.

Figure 2F:
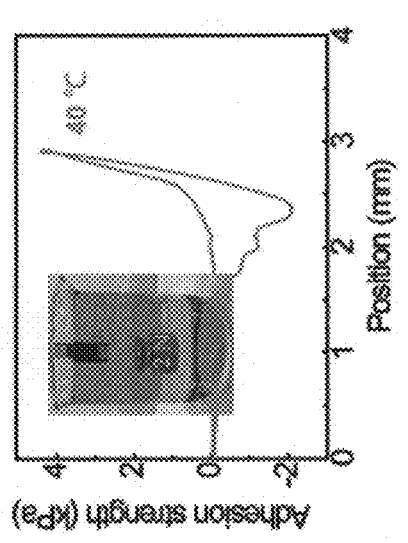
Figure 2G:
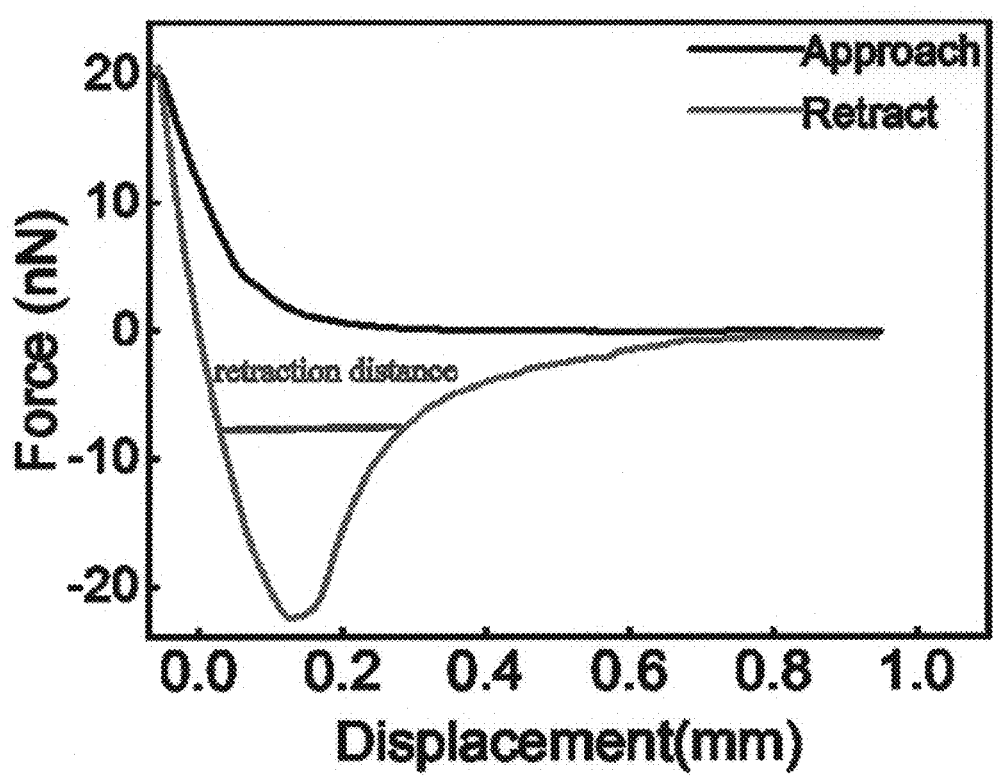

As can be envisaged, this remarkable microscopic adhesion property can be translated into exceptional collective adhesion properties. With a view of characterizing the adhesive properties at a macroscopic level, experiments were conducted by depositing a uniform layer of adhesive on a silicon substrate with a size of 1.5 cm×1.5 cm and then measuring its underwater adhesion strength using high-sensitive universal testing machine. Please see FIGS. 9A and 9B. The macroscopic adhesion strength of the adhesive coating against the target surface at 40° C. is ~20 folds larger than that at 25° C. Please also see FIGS. 2D and 2E. This is consistent with that obtained in the microscopic characterization. Such an underwater adhesion strength is 5 times larger than that of a convention (3M) double-sided tape. Please see FIG. 10. It is to be noted that at 40° C. the wet adhesion can be further dramatically amplified by applying the pre-loading to repel the surrounding water film between the adhesive and the adhered surface. Please see FIG. 10. This is consistent with the macroscopic measurement, in that there is no marked degradation in the adhesion strength after many cycles of measurement and confirm that the wet adhesion is fully reversible. Please see FIG. 2F. FIG. 2F is a graph showing reversible control of underwater adhesion through the control of the temperature on the adhesive. Although the specific response time to switch the interfacial adhesion is not quantitatively measured, it is shown that it is only limited by the speed in the temperature control. Taken together, when compared with previous approach using chemical control which entails a longer response time, the adhesion of the present adhesive system can be dynamically mediated in a more flexible and faster manner.

Figure 12:
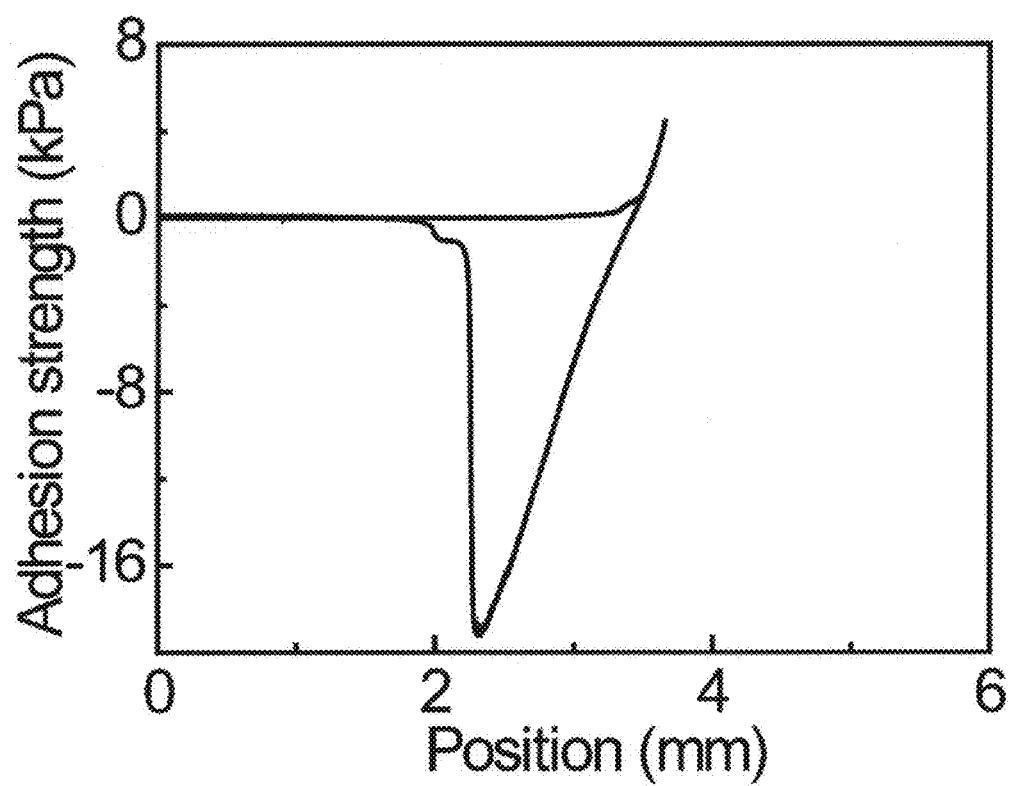
FIG. 12 is a graph showing adhesion strength of the adhesive coating in the air, in that the adhesion strength of the adhesive coating at 25° C. and 40° C. in air is ~20 kPa, which barely shows any difference, demonstrating that the thermo-reversible adhesion cannot be achieved in dry condition.

To elucidate the intriguing wet adhesion capability, further characterization studies were conducted seeking to measure the adhesion strength in response to different temperature triggers in dry condition. It was found that there was no marked difference in the adhesion strength under room temperature and 40° C. Please see FIG. 12. FIG. 12 is significant in that it illustrates a striking contrast to the reversible adhesion observed in the wet environment. This suggests that the wet adhesion should be intricately reliant on the interaction with the water phase. Indeed, in the wet environment at room temperature, the pNIAPM side-chains on the adhesive surface can easily form intermolecular hydrogen bonding with adjacent water molecules. Please see FIG. 3A. FIG. 3A is a schematic diagram showing the screening of the interfacial adhesion when the local temperature of the adhesive is below LCST. In this condition, the pNIPAM can easily form intermolecular hydrogen bonding with adjacent water molecules and the infused water layer transforms the pNIPAM side-chains to a swelling state. As a result of selective recognition between the host and guest copolymers, the adhesive moiety DOPA is spatially stabilized and confined underneath the swelling pNIPAM chains, screening the interfacial interaction of the adhesive moiety DOPA with target surface. As a result, the infused water serves as a lubricating film and transforms the pNIPAM into a swelling state with a global hydrophilic property with a water CA of 41°.

FIG. 3B is a TEM image showing the homogenous dispersion of the pNIPAM-CD without the occurrence of aggregation at room temperature. The adhesive surface exhibits a global hydrophilic property with a water CA of 41° (inset). As shown in this figure, TEM measurement also reveals that the host pNIPAM-CD displays a homogeneous state without the occurrence of aggregation. Moreover, as a result of the specific host-guest chemistry, the adhesive moiety DOPA is spatially confined and stabilized underneath the swelling pNIPAM side-chains, thereby the interfacial interaction between DOPA and target surface is dramatically screened.

FIG. 3C is a schematic diagram showing activation of the adhesiveness of the system. When the temperature is above LCST, intramolecular hydrogen bonding inside the pNIPAM chains is formed, thus reactivating the interfacial adhesion. FIG. 3D is an image showing that when the pNIPAM-CD chains are collapsed at the supramolecular level, this is also associated with the formation of numerous agglomerates during the phase transition. As a result, the adhesive group is exposed, leading to pronounced interfacial adhesion. In this condition, the water CA at 40° C. is increased to ~82° (inset). Thus, when exposed to an external temperature above LCST, the intramolecular hydrogen bonding of the pNIPAM with adjacent water molecules is broken down (FIG. 3C), and hence the swelling state displayed at room temperature is collapsed as evidenced by the formation of numerous agglomerates during the phase transition (FIG. 3D). Accordingly, the adhesive moiety DOPA re-emerges from the pNIPAM, re-activating the interfacial interaction. The intramolecular transformation at the supramolecular level is also associated with the marked variation in the wettability at a global scale. As shown in FIG. 3D, at 40° C., the water contact angle on the adhesive coating is increased to ~82°, which is in striking contrast to the hydrophilic property at room temperature. Please also see FIGS. 13C-13D. It can thus been understood that the wet adhesion activity can be dynamically regulated by screening or activating the interfacial interaction using a simple temperature trigger.

Figure 4A:
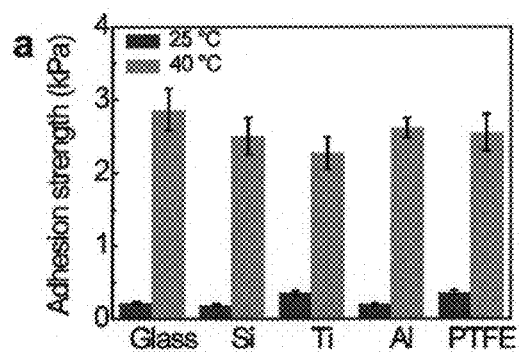
FIGS. 4A to 4D are graphs and diagrams illustrating versatility and generality of the adhesive system of FIGS. 1A to 1D.
Figure 4B:
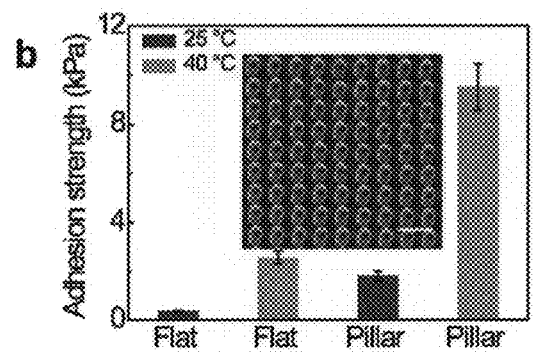

In order to demonstrate the versatility and generality of the present invention, quantification studies were also performed. In particular, the adhesion strength of the as-synthesized coating against wide-ranging solid substrates including inorganic (glass, silicon, titanium, aluminum) and organic surfaces (PDMS, PTFE) were determined. Referring to FIG. 4A, it is illustrated that the wet adhesion strength on various substrates are comparable, suggesting that the interfacial adhesion is independent of target materials. Moreover, the wet adhesion strength can be further amplified by depositing the as-prepared adhesive on gecko-like surfaces. FIG. 4B is a SEM image showing patterned PDMS post arrays with post diameter and height of 5 and 10 μm, respectively. Unlike the gecko which loses its adhesive property in water or high humidity surrounding, it is shown that the adhesive strength on compliant post arrays at both 25 and 40° C. is much larger than that on the flat surface owing to the enlarged effective contact area.

Figure 4C:
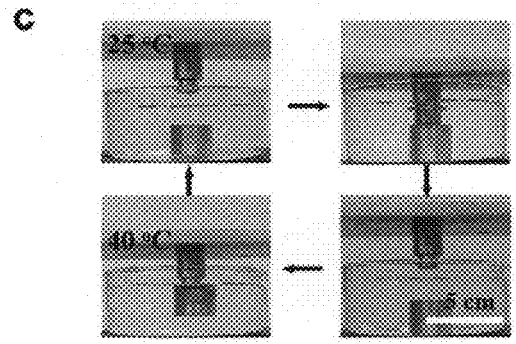
Figure 4D:
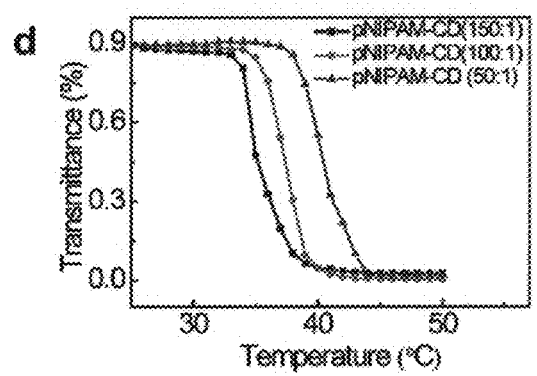

Studies were also carried out to demonstrate the utility of the as-synthesized adhesive system for the controlled pick-and-place of an object in an aqueous environment. Referring to FIG. 4C, by adjusting the local adhesive temperature above or below LCST with a heat conducting aluminum sheet, the interfacial adhesion can be activated or screened, allowing a metal block weighted ~200 g to be transported to and released at any preferential location. The setting time to switch the adhesion for pick-and-place can be arbitrarily controlled to fit specific applications. Moreover, as discussed earlier, the LCST of the adhesive system in the form of a coating applied can be predicted and modulated without a marked alternation of the adhesive property. As shown in FIG. 4D, the LCST can be changed between 32° C. and 40° C. by controlling different pNIPAM to CD monomer proportion. Thus, the tunability in the switching temperature, adhesion strength as well as the setting time to rectify the adhesion can be leveraged to engineer novel bio-adhesives that are capable of automatically responding to environmental stimuli, thus yielding smarter synthetic materials that satisfy application-specific requirements. Moreover, such an adhesive can be deposited to curved and flexible substrates and small flying micro-robots for on-demand perching and adhesion without the cost and up-scaling concerns to achieve appealing functions which are unrealized using the conventional glues.

More in-depth details of the experiments carried out with respect to the present invention are as follows.

Materials and Methods

1. Chemicals

Dopamine hydrochloride (DOPA-HCl) (>98%), methoxyethyl acrylate (MEA) (95%) 1-Adamantanecarboxylic acid chloride 98%), 2,2'-azobisisobutyronitrile (AIBN, 98%), hexane (99%), tetrahydrofuran (THF) and anhydrous dimethyl formamide (DMF) are purchased from Sigma-Aldrich. Sodium borate, ethyl acetate, sodium bicarbonate, magnesium sulfate, and sodium hydroxide are purchased from Meyer. Before utilization, methacrylate anhydride is passed through a column packed with $Al_2O_3$ to remove inhibitor, and AIBN is recrystallized twice from methanol.

2. Copolymers Synthesis 2.1. Synthesis of Guest Copolymer pDOPA-AD-MEA

The synthesis of the guest copolymer pDOPA-AD-MEA involves the synthesis of DOPA monomer, AD monomer and their copolymerization. Please see FIG. 5A. The experimental details for the synthesis are given below.

Synthesis of DOPA Monomer.

The DOPA monomer is synthesized from DOPA-HCl according to a previously described procedure with slight modifications. Briefly, 10 g of sodium borate and 4 g of $NaHCO_3$ were first dissolved in 100 ml of deionized water and bubbled with $N_2$ for 20 minutes. Then 5 g of DOPA-HCl (26.4 mmol) was added, followed by the dropwise addition of 4.7 ml of MEA (29 mmol) in 25 ml of THF, during which the pH of solution was kept above 8 with the addition of 1M NaOH as necessary. The reaction mixture was stirred overnight at room temperature with $N_2$ bubbling. The aqueous mixture was washed twice with 50 ml of ethyl acetate and then the pH of the aqueous solution was reduced to less than 2 and extracted with 50 ml of ethyl acetate for three times. The final three ethyl acetate layers were combined and dried over $MgSO_4$ to reduce the volume to around 25 ml. 200 ml of hexane was added with vigorous stirring and the suspension was held at 4° C. overnight. The crude product was dried and purified by recrystallization from hexane to obtain the compound as a gray solid.

Synthesis of AD Monomer.

The AD monomer is prepared with adamantanecarboxylic acid chloride in anhydrous methylene chloride. Specifically, 30 ml of anhydrous methylene chloride was added to a 200 ml round-bottom flask as a solvent and bubbled with $N_2$ at 0° C. for 20 minutes. Subsequently, 5.94 g of adamantanecarboxylic acid chloride and 5 ml of triethylamine were dissolved separately in the degassed anhydrous methylene chloride. Then 5.216 g of 2-hydroxyethyl methacrylate (0.04 mol) was dissolved into 20 ml of anhydrous methylene chloride, and added into the reaction solution dropwise. The reaction mixture was agitated for 4 h at 0° C. The crude material was dissolved in 100 ml hydrochloric acid, and the solution was washed with saturated sodium carbonate solution until a neutral pH was reached. Subsequently, methylene chloride was removed using a rotavap, the crude product was purified by Biotage Isolera TM Prime automatic column chromatography (Biotage SNAP 50 g silica column; methylene chloride/methyl alcohol 10:1 to gradient; flow rate 1440 m l/m in) to obtain as a yellowish liquid.

Synthesis of Guest Copolymer pDOPA-AD-MEA.

The adhesive guest copolymer pDOPA-AD-MEA is synthesized via free radical copolymerization from DOPA monomer, AD monomer, and MEA at the atmosphere of nitrogen gas to protect the product from oxidation. Please see FIG. 5A. In detail, 1 g of DOPA monomer, 4 g of MEA, and 1.5 g of AD monomer were dissolved separately in 15 ml of degassed DMF in a 100 ml round bottom flask under the atmosphere of nitrogen. The solutions were stirred at room temperature for 20 minutes to obtain the homogenous solution. Then 60 mg of AIBN was added into the solution. After three repeats of the degassing procedure (freeze-vacuum-thaw-nitrogen purging), the reaction mixture was agitated for 12 h at 80° C. Subsequently, DMF was removed using a rotary evaporator, the crude product was dissolved in 5 ml of THF, and purified by three repeats of precipitation in 50 ml of ethyl alcohol at 4° C. using a centrifuge at 8000 rpm for 30 minutes. The copolymer was obtained as grey, sticky solid.

2.2 Synthesis of the Host Copolymer pNIPAM-CD

Host copolymer pNIPAM-CD is prepared by the free radical polymerization of N-Isopropylacrylamide and amino-β-Cyclodextrin with AIBN as the initiator. Please see FIG. 5B. Briefly, 2.26 g of N-Isopropylacrylamide and 30 mg of glycidyl methacrylate were dissolved separately in 10 ml of degassed DMF in a 50 ml Schlenk flask under nitrogen protection and stirred at room temperature for 1 h to obtain a homogenous solution. Subsequently, 20 mg AIBN was added to the solution with the protection of nitrogen. After 4 h polymerization at 80° C., 0.2 g of amino-β-Cyclodextrin was imbursed into the reaction solution and agitated for another 10 h at 80° C. for the copolymerization of guest copolymer pNIPAM-CD. The crude product was then purified in 30 ml of hot water using centrifuge at 10,000 rpm for 20 minutes.

2.3 Preparation of the Adhesive Coating

To prepare the adhesive coating for the characterization of the adhesion strength, a silicon substrate is first thoroughly cleaned in Piranha solution containing sulfuric acid (97% $H_2SO_4$) and hydrogen peroxide. Then the clean silicon substrate is first dip-coated in an ethanol solution of pDOPA-AD-MEA (5 mg/ml) for ~20 min at 70° C., followed by immersion into pNIPAM-CD solution (5 mg/ml) for the self-assembly of the host copolymer pNIPAM-CD with a duration of 30 min~120 min.

3. Characterizations

The copolymer composition is determined by $^1$H NMR (400 MHz) analysis using Varian VNMRS 400 MHz spectrometer in dimethyl sulfoxide (DMSO). Surface element component is analyzed by X-ray photoelectron spectroscopy (XPS, ESCALAB 250Xi multifunctional spectrometer, Thermo Fisher) using Al Kα radiation. Attenuate total reflection infrared (ATR-IR) spectrum is measured using a Nicolet iS10 instrument (Thermal Nicolet Corporation). UV-vis absorption spectrum of the pNIPAM-CD is recorded on UV2600 spectrometer (SHIMADZU). The sessile water droplet contact angle (CA) measurement is conducted using a DSA-100 optical contact angle meter (Kruss Company, Ltd., Germany) at 25° C. and 40° C., respectively. Scanning electron microscope (SEM) images are obtained on a JSM-6701F field emission scanning electron microscope (FE-SEM) at 5-10 kV. The microscopic underwater adhesion property is quantified using an AFM integrated with a temperature controller (Bruker Optics). The macroscopic adhesion is measured using a high-sensitive universal testing machine (UTM, SHIMADZU, EZ-LX).

3.1. Characterization of the As-Prepared Copolymers

We analyze the chemical structure of the host and guest copolymers by $^1$H NMR (400 MHz). The functional chemical structures of the host and guest copolymers as well as their corresponding NMR peaks are labeled in FIGS. 6A and 6B. The characteristic NMR peak of adamantine group (b, 1.8 ppm) and phenolic hydroxyl group (f, 6.6 ppm) in the pDOPA-AD-MEA can be easily identified (FIG. 6A). Similarly, FIG. 6B shows the characteristic NMR peaks of the pNIPAM-CD, which contains the cyclodextrin hydroxyl group (e, 3.5 ppm and f, 3.8 ppm) and imino group (7.25 ppm). In terms of the FTIR spectra measurement, the absorption peaks at 3430 $cm^{-1}$, 1730 $cm^{-1}$, and 1170 $cm^{-1}$ are assigned to the phenolic hydroxyl group, ester acyl group, and benzene group, respectively (FIG. 7A). The absorption peaks at 3290 $cm^{-1}$, 2970 $cm^{-1}$, 1660 $cm^{-1}$, and 1560 $cm^{-1}$ are ascribed to cyclodextrin hydroxyl group, methyl-methylene group, carbonyl group, and imino group, respectively (FIG. 7B). All these measurements demonstrate the successful synthesis of pDOPA-AD-MEA and pNIPAM-CD, respectively.

3.2. Characterization of the as-Prepared Adhesive Coating

Figures 8A, 8B:
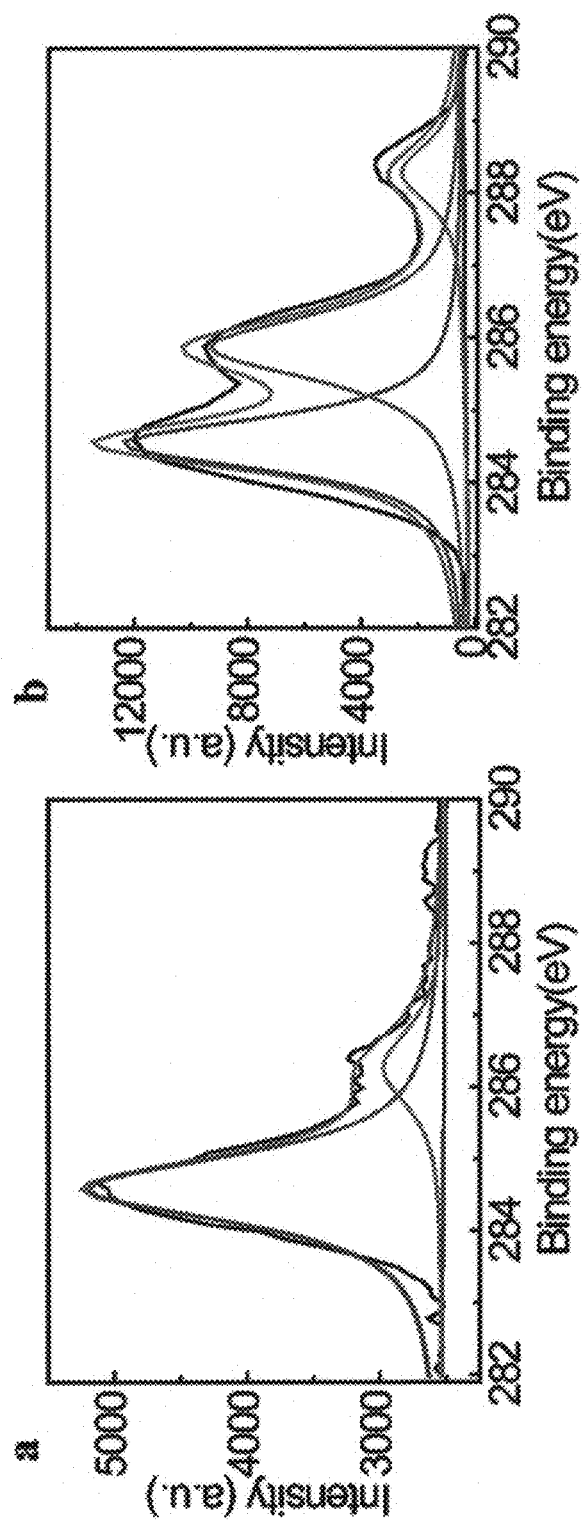
FIGS. 8A and 8B are graphs of high-resolution C1s XPS spectrum analysis of host copolymer and the adhesive coating, in which intense peaks at 284.8 eV and 286.3 eV observed in the XPS spectrum of FIG. 8A are assigned to C1s absorption of the ether group in pDOPA-AD-MEA.

We analyze the surface element component by XPS using Al Kα radiation. As shown in the XPS spectrum of the guest copolymer (FIGS. 8A and 8B), the intense peaks at 284.8 and 286.3 eV are ascribed to the C1s absorption of ether group in pDOPA-AD-MEA. By contrast, an additional intense peak at 288.3 eV emerges upon the self-assembly of host copolymer, which is ascribed to the carbonyl amide group in pNIPAM-CD, indicating the successful assembly of pNIPAM-CD onto the adhesive guest copolymer through the host-guest chemistry (FIG. 8B). Moreover, the successful preparation of the adhesive coating on the silicon substrate is also evidenced by the substantial increase in the contents of C and N elements displayed by the adhesive coating as opposed to that by the bare silicon substrate. Please see Table 1 above.

4. Adhesion Measurement

Figure 10:
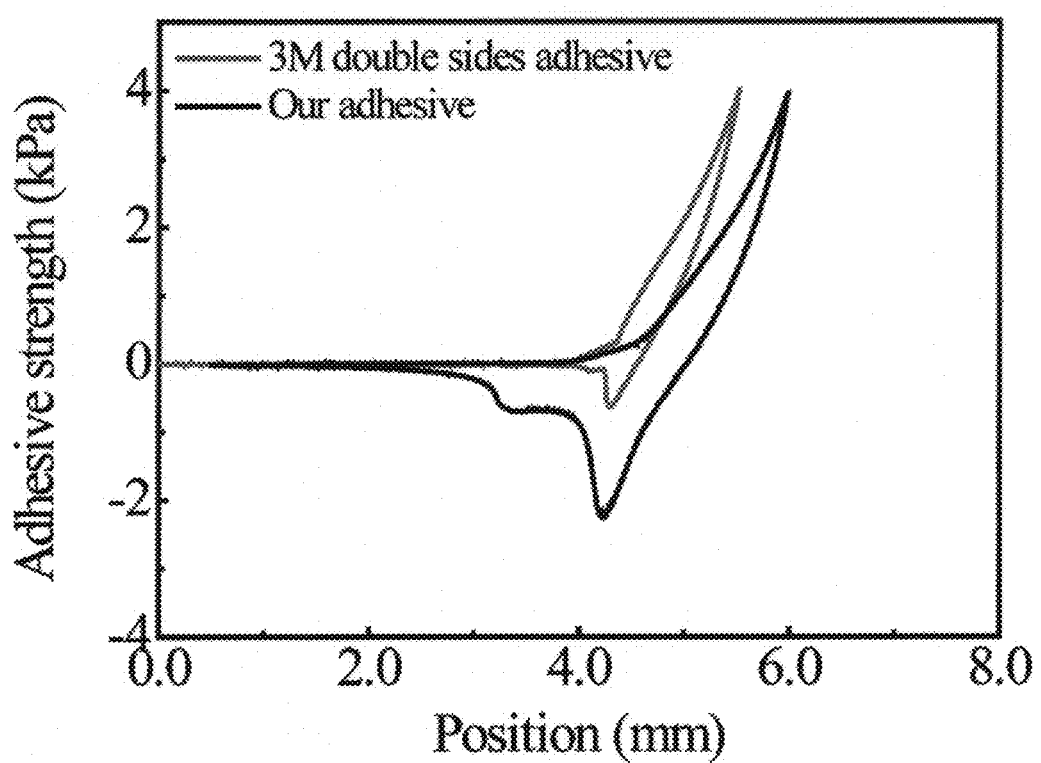
FIG. 10 is a graph showing the underwater adhesion performance of adhesive coating and 3M double-sided tape, in that in the wet environment, the adhesion strength of the adhesive system in accordance with the present invention is 5 times stronger than that of commercially available 3M double-sided tape.

To allow for the characterization of the adhesion behaviors in response to different temperatures, we measure the wet adhesion at the microscopic level using an AFM integrated with a temperature controller. The underwater adhesion strength at the macroscopic level is measured by UTM (please see FIGS. 9A and 9B), which is widely utilized to measure the interaction force between a wide range of surfaces including polymers, hydrogels, and inorganic materials et al. To provide a wet environment, we deign a small chamber to encapsulate the adhesive and target surfaces. Briefly, the silicon substrate decorated with the adhesive coating is tightly fixed to the designed chamber and a thoroughly cleaned silicon substrate is used as the target surface. After compressed for 10 s with the applying a load of 1N f, two surfaces are separated and the interfacial adhesion strength is then measured. The local temperature of the adhesive coating is controlled by the temperature controller which is fixed on the equipment. For comparison, the underwater adhesion strength of the commercially available 3M double-sided tape was measured. As shown in FIG. 10, the underwater adhesion strength of the 3M double-sided tape is ~0.5 kPa, which is 5 times smaller than that of our adhesive.

Figures 11A, 11B, 11C:
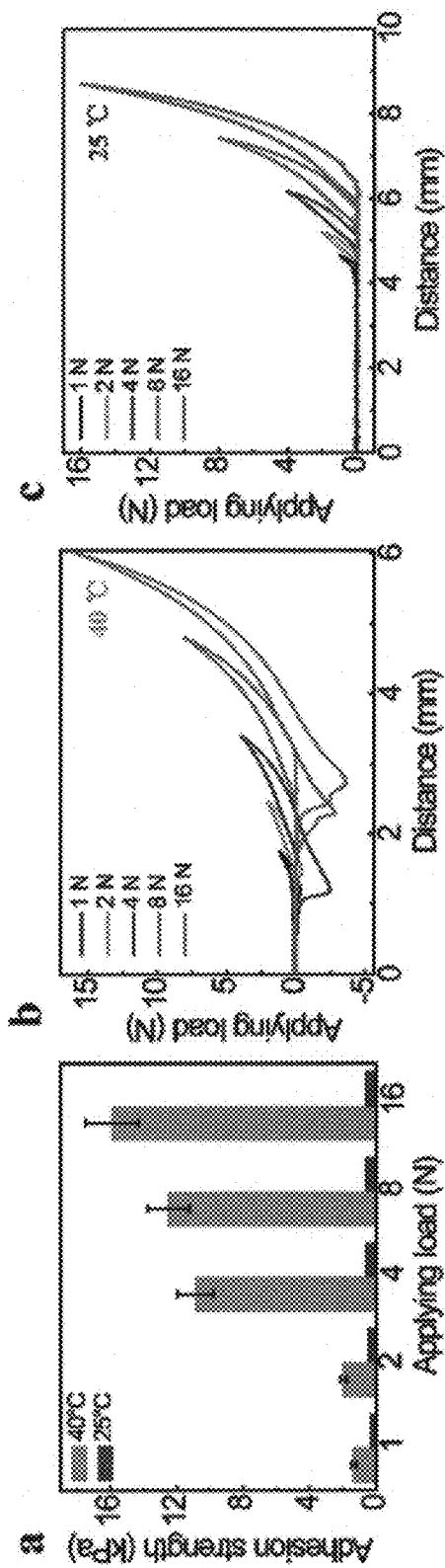
FIGS. 11A, 11B and 11C are graphs showing tailoring underwater adhesion by applying load, in which in FIG. 11A, the adhesion strength of the adhesive coating under different applying load, and in FIGS. 11B and 11C, the adhesion force curve of the adhesive coating under various applying load at 40° C. and 25° C., respectively.

It was found that the adhesion strength is also sensitive to the applying load. At 40° C., it is observed that the underwater adhesion strength increases dramatically with the augment of the applying load (please see FIGS. 11A and 11B). The adhesion strength jumps to 11 kPa when the applying load is increased to 4 N as a result of enhanced contact area between the adhesive molecules and target surface. By contrast, at 25° C. there is no marked variation in the adhesion strength with the increase of the applying load, even up to 16 N (please see FIGS. 11A and 11C).

To elucidate the intriguing wet adhesion capability, further characterization studies were conducted to determine the adhesion strength in response to different temperatures in a dry condition. It was found that the adhesion strength of the adhesive coating at 25° C. and 40° C. is almost the same, which is in striking contrast to the reversible adhesion observed in the wet environment. Also such a strength is much larger than the underwater adhesion strength at 40° C. (please see FIG. 12). These results suggest that the reversible wet adhesion should be intricately reliant on the interaction with the water phase.

5. Wettability of the Adhesive Coating

Figure 13A:
FIGS. 13A, 13B, 13C and 13D are schematic diagrams showing contact angle measurement, in that in FIG. 13A there is shown water contact angle measurement of a thoroughly cleaned Silicon substrate, in FIG. 13B there is shown the water contact angle increased to 92° after the deposition of the pDOPA-AD-MEA due to the existence of hydrophobic MEA monomer in the guest copolymer, in FIG. 13C there is shown after the assembly of pNIPAM-CD the water contact angle at 25° C. reduced to 41°, and in FIG. 13D at 40° C. the surface becomes hydrophobic with a CA of 82° due to the collapse of pNIPAM side-chains.
Figure 13B:
Figure 13D:
Figure 13C:
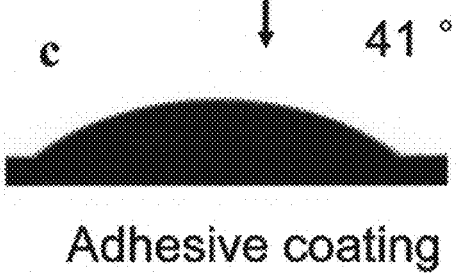

To underpin the mechanism for the peculiar adhesion switching in response to different temperatures, we quantify the wettability of the as-prepared adhesive coating. As illustrated in FIGS. 13A to 13D, a flat silicon substrate is hydrophilic with a water contact angle (CA) of 45° (FIG. 13A). With the deposition of a guest copolymer pDOPA-AD-MEA onto the silicon substrate, the water CA is increased to 92° (FIG. 13B). Surprisingly, the wettability of the adhesive surface which is prepared through the host-guest molecule recognition is highly dependent on the temperature. At 25° C., the adhesive surface exhibits a water CA of 41° and when the temperature is increased to 40° C. (above LCST), the water CA is 82° (FIGS. 13C and 13D). Such a distinct variation in the global wettability property is due to the structural transformation at the supramolecular level. At room temperature, the pNIPAM side-chains on the adhesive surface can easily form intermolecular hydrogen bonding with adjacent water molecules. As a result, the infused water serves as a lubricating film and transforms the pNIPAM into a swelling state with a global hydrophilic property. When exposed to an external temperature above LCST, the intramolecular hydrogen bonding of the pNIPAM with adjacent water molecules is broken down, and leading to the hydrophobic property as observed in our experiment.

It should be understood that certain features of the invention, which are, for clarity, described in the content of separate embodiments, may be provided in combination in a single embodiment. Conversely, various features of the invention which are, for brevity, described in the content of a single embodiment, may be provided separately or in any appropriate sub-combinations. It is to be noted that certain features of the embodiments are illustrated by way of non-limiting examples. It is also to be noted that certain features in connection with the invention are not explained in great detail for brevity reason. However, such features are readily understood by a skilled person in the art. For example, a skilled person would understand that the automation of the system can be achieved by linked different components in the systems. Also, a skilled person in the art will be aware of the prior art which is not explained in the above for brevity purpose.

REFERENCE

The following references are incorporated in their entirety and a skilled person is considered to be aware of disclosure of these references.

1 Waite, J. H. Adhesion a la moule. *Integr. Comp. Biol.* 42, 1172-1180 (2002).
2 Rose, S. et al. Nanoparticle solutions as adhesives for gels and biological tissues. *Nature* 505, 382-385 (2014).
3 Ahn, Y, Jang, Y, Selvapalam, N., Yun, G. & Kim, K. Supramolecular velcro for reversible underwater adhesion. *Angew. Chem.* 125, 3222-3226 (2013).
4 Lee, H., Scherer, N. F. & Messersmith, P. B. Single-molecule mechanics of mussel adhesion. *Proc. Natl. Acad. Sci. USA* 103, 12999-13003 (2006).
5 Heinzmann, C., Weder, C. & Espinosa, L. M. Supramolecular polymer adhesives: advanced materials inspired by nature. *Chem. Soc. Rev.* 45, 342-358 (2016).
6 Jones, J. P., Sima, M., O'hara, R. G. & Stewart, R. J. Water-Borne Endovascular Embolics Inspired by the Undersea Adhesive of Marine Sandcastle Worms. *Adv. Healthcare Mater.* 5, 795-801 (2016).
7 Lee, B. P., Messersmith, P. B., Israelachvili, J. N. & Waite, J. H. Mussel-inspired adhesives and coatings. *Annu. Rev. Mater. Res.* 41, 99-132 (2011).
8 Lee, H., Dellatore, S. M., Miller, W. M. & Messersmith, P. B. Mussel-inspired surface chemistry for multifunctional coatings. *Science* 318, 426-430 (2007).
9 Fichman, G. et al. Seamless metallic coating and surface adhesion of self-assembled bioinspired nanostructures based on di-(3,4-dihydroxy-1-phenylalanine) peptide motif. *ACS nano* 8, 7220-7228 (2014).
10 Lee, H., Lee, B. P. & Messersmith, P. B. A reversible wet/dry adhesive inspired by mussels and geckos. *Nature* 448, 338-341 (2007).
11 Ahn, B. K. et al. High-performance mussel-inspired adhesives of reduced complexity. *Nat. Commun.* 6, 8663 (2015).
12 North, M., Grosso, C. A. & Wilker, J. J. High Strength Underwater Bonding with Polymer Mimics of Mussel Adhesive Proteins. *ACS Appl. Mater. Interfaces* 9, 7866-7872 (2017).
13 Lim, C. et al. Nanomechanics of Poly (catecholamine) Coatings in Aqueous Solutions. *Angew. Chem., Int. Ed.* 55, 3342-3346 (2016).
14 Shin, M. et al. Complete prevention of blood loss with self-sealing haemostatic needles. *Nat. Mater* 16, 147-152 (2017).
15 Yang, S. Y. et al. A bio-inspired swellable microneedle adhesive for mechanical interlocking with tissue. *Nat. Commun.* 4, 1702 (2013).
16 Zeng, H. et al. Adhesion and Detachment Mechanisms between Polymer and Solid Substrate Surfaces: Using Polystyrene-Mica as a Model System. *Macromolecules* 49, 5223-5231 (2016).
17 Zhao, Q. et al. Underwater contact adhesion and microarchitecture in polyelectrolyte complexes actuated by solvent exchange. *Nat. Mater* 15, 407-412 (2016).
18 Maier, G. P., Rapp, M. V., Waite, J. H., Israelachvili, J. N. & Butler, A. Adaptive synergy between catechol and lysine promotes wet adhesion by surface salt displacement. *Science* 349, 628-632 (2015).
19 Kim, T. i., Jeong, H. E., Suh, K. Y. & Lee, H. H. Stooped Nanohairs: Geometry-Controllable, Unidirectional, Reversible, and Robust Gecko-like Dry Adhesive. *Adv. Mater.* 21, 2276-2281 (2009).
20 Michal, B. T., Spencer, E. J. & Rowan, S. J. Stimuli-Responsive Reversible Two-Level Adhesion from a Structurally Dynamic Shape-Memory Polymer. *Acs. Appl. Mater Interfaces* 8, 11041-11049 (2016).
21 Wang, Y. et al. Switchable Dry Adhesion with Step-like Micropillars and Controllable Interfacial Contact. *Acs. Appl. Mater. Interfaces* 8, 10029-10037 (2016).
22 Ye, Z., Lum, G. Z., Song, S., Rich, S. & Sitti, M. Phase Change of Gallium Enables Highly Reversible and Switchable Adhesion. *Adv. Mater* 28, 5088-5092 (2016).
23 Reddy, S., Arzt, E. & Campo, A. Bioinspired surfaces with switchable adhesion. *Adv. Mater* 19, 3833-3837 (2007).
24 Narkar, A. R., Barker, B., Clisch, M., Jiang, J. & Lee, B. P. pH Responsive and Oxidation Resistant Wet Adhesive based on Reversible Catechol-Boronate Complexation. *Chem. Mater* 28, 5432-5439 (2016).
25 Zeng, H., Hwang, D. S., Israelachvili, J. N. & Waite, J. H. Strong reversible $Fe^{3+}$-mediated bridging between dopa-containing protein films in water. *Proc. Natl. Acad. Sci. USA* 107, 12850-12853 (2010).
26 Zhong, C. et al. Strong underwater adhesives made by self-assembling multi-protein nanofibres. *Nat. Nanotechnol.* 9, 858-866 (2014).
27 Deshmukh, S. A., Sankaranarayanan, S. K., Suthar, K. & Mancini, D. C. Role of solvation dynamics and local ordering of water in inducing conformational transitions in poly (N-isopropylacrylamide) oligomers through the LCST. *J. Phys. Chem. B* 116, 2651-2663 (2012).
28 Abbott, L. J., Tucker, A. K. & Stevens, M. J. Single Chain Structure of a Poly (N-isopropylacrylamide) Surfactant in Water. *J. Phys. Chem. B* 119, 3837-3845 (2015).
29 Puthoff, J. B., Prowse, M. S., Wilkinson, M. & Autumn, K. Changes in materials properties explain the effects of humidity on gecko adhesion. *J. Exp. Biol.* 213, 3699-3704 (2010).
30 Stark, A. Y. et al. Surface wettability plays a significant role in gecko adhesion underwater. *Proc. Natl. Acad. Sci. USA* 110, 6340-6345 (2013).

The invention claimed is:
1. An adhesive system operable in a wet environment and with temperature-dependent adhesiveness characteristics, comprising a guest copolymer portion and a host copolymer portion reversibly bindable with the guest copolymer portion, wherein:

the guest copolymer portion including 3,4-dihydroxy-L-phenylalanine (DOPA) acting as an adhesive moiety, a recognition molecule and a hydrophobic molecule connecting the adhesive moiety and the recognition molecule;

the host copolymer portion including a macrocyclic host molecule from a host family of supramolecules for specifically binding with the guest copolymer at the recognition molecule, and a polymer with temperature dependent wettability;

the guest copolymer portion and the host copolymer portion are adapted to assume a first configuration in which the guest copolymer portion and the host copolymer portion are bonded together and, at or below a predetermined temperature, the adhesive moiety of the guest copolymer is screened by a water layer absorbed by a chain from the temperature dependent wettability polymer, thus hindering adhesiveness of the adhesive system;

the guest copolymer portion and the host copolymer portion are adapted to assume a second configuration in which, at a temperature above the predetermined temperature, the adhesive moiety of the guest copolymer is not screened by water due to collapsing of the chain of the temperature dependent wettability polymer, thus releasing the adhesive moiety of the guest copolymer in order to allow the adhesiveness of the adhesive system to emerge;

the recognition molecule is adamantine (AD) or ammonium salt (ANS); and the macrocyclic host molecule is cyclodextrin (CD) or cucurbituril (CB).

2. A system as claimed in claim 1, wherein the temperature-dependent wettability polymer is selected from the group consisting of poly(N-isopropylacrylamide (p-NIPAM), poly(N, N-diethyl acrylamide) (p-DEAAM), poly(N-(D L)-(1-hydroxymethyl) propylmethacrylamide) (p-(DL)-HMPMA), poly(dimethylaminoethyl methacrylate) (p-DMAEMA), and poly(N-vinylcaprolactone) (p-VCL).

3. A system as claimed in claim 2, wherein the temperature-dependent wettability polymer is poly(N-isopropylacrylamide (p-NIPAM).

4. A system as claimed in claim 1, wherein the predetermined temperature is dependent on the ratio of poly(N-isopropylacrylamide (p-NIPAM) to cyclodextrin (CD) in the host copolymer.

5. A system as claimed in claim 4, wherein the ratio of poly(N-isopropylacrylamide (p-NIPAM) to cyclodextrin (CD) is substantially 150:1 (n:n, molar ratio), whereby the predetermined temperature is substantially 35° C.

6. A system as claimed in claim 1, wherein the system is adapted with an adhesiveness characteristic independent surrounding pH condition.

* * * * *